(12) United States Patent
Arima

(10) Patent No.: US 11,772,332 B2
(45) Date of Patent: Oct. 3, 2023

(54) WEB WELDING SYSTEM AND WELDING METHOD

(71) Applicant: ZUIKO CORPORATION, Osaka (JP)

(72) Inventor: Takashi Arima, Osaka (JP)

(73) Assignee: ZUIKO CORPORATION, Osaka (JP)

( * ) Notice: Subject to any disclaimer, the term of this patent is extended or adjusted under 35 U.S.C. 154(b) by 95 days.

(21) Appl. No.: 17/609,649

(22) PCT Filed: May 12, 2020

(86) PCT No.: PCT/JP2020/018973
§ 371 (c)(1),
(2) Date: Nov. 8, 2021

(87) PCT Pub. No.: WO2020/241245
PCT Pub. Date: Dec. 3, 2020

(65) Prior Publication Data
US 2022/0212415 A1 Jul. 7, 2022

(30) Foreign Application Priority Data
May 24, 2019 (JP) ................................. 2019-097469

(51) Int. Cl.
*B29C 65/08* (2006.01)
*B29C 65/00* (2006.01)
*B29L 31/48* (2006.01)

(52) U.S. Cl.
CPC ............ *B29C 65/08* (2013.01); *B29C 66/41* (2013.01); *B29C 66/73921* (2013.01); *B29L 2031/4878* (2013.01)

(58) Field of Classification Search
CPC .. B29C 65/08; B29C 65/086; B29C 66/73921
(Continued)

(56) References Cited

U.S. PATENT DOCUMENTS 6,338,769 B1 * 1/2002 Rabasa ................... B32B 37/22
156/289
7,449,084 B2 * 11/2008 Nakakado ......... B29C 66/93441
156/73.1
(Continued)

FOREIGN PATENT DOCUMENTS

WO 2005005296 A1 1/2005
WO 2005080065 A1 9/2005
(Continued)

OTHER PUBLICATIONS

International Search Report for corresponding Application No. PCT/JP2020/018973, dated Jul. 21, 2020.

*Primary Examiner* — James D Sells
(74) *Attorney, Agent, or Firm* — Renner, Otto, Boisselle & Sklar, LLP

(57) ABSTRACT

The present welding system includes: a transport device that transports a work in a state where a plurality of webs are overlaid on each other; an anvil roller that includes an anvil which intermittently makes contact with the first surface of the work being transported; an ultrasonic horn that is opposite the second surface of the work and that cooperates with the anvil to apply vibration energy to the work so as to intermittently weld the webs; a speed changing device that lowers the transport speed of the work supplied between the horn and the anvil when the welding is performed; and a pressing device that presses the first surface of the work to the anvil when the welding is performed.

13 Claims, 3 Drawing Sheets

(58) Field of Classification Search
USPC .......................................................... 156/73.1
See application file for complete search history.

(56) References Cited

U.S. PATENT DOCUMENTS

| | | |
|---|---|---|
| 9,186,845 B2 * | 11/2015 | Shimada ............. B29C 66/8432 |
| 2008/0236756 A1 | 10/2008 | Nakakado |
| 2015/0298390 A1 | 10/2015 | Shimada |
| 2015/0328055 A1 | 11/2015 | Shimada |

FOREIGN PATENT DOCUMENTS

| | | |
|---|---|---|
| WO | 2014077152 A1 | 5/2014 |
| WO | 2014097636 A1 | 6/2014 |

* cited by examiner

WEB WELDING SYSTEM AND WELDING METHOD

TECHNICAL FIELD

The present invention relates to web welding systems and welding methods mainly for wearing articles.

BACKGROUND ART

A welding system is known in which in order to seal (weld) a plurality of webs for each disposable article unit, a pair of ultrasonic horns and a pair of anvils are provided (patent literatures 1 to 3).

In the conventional technique described above, the webs which are overlaid on each other are transported, are passed between the horn of an ultrasonic device and an anvil roller, are intermittently sandwiched between an anvil formed on the outer circumference of the anvil roller and the horn and are intermittently welded together.

CITATION LIST

Patent Literature

Patent Literature 1: WO 05/005296 A1 (front page)
Patent Literature 2: WO 05/080065 A1 (front page)
Patent Literature 3: WO 14/077152 A1 (front page)

SUMMARY OF INVENTION

In the conventional technique described above, since a welding time is sufficiently taken when the webs are welded, the transport speed of the webs is periodically changed such that the transport speed is lowered.

However, the transport speed is changed as described above, and thus it is inevitable that the webs flutter or expand and contract. In particular, in the case of wearing articles, the thickness of part of an absorbent core is increased and is uneven, and thus the flutter easily occurs. In a case where the material of the webs is unlikely to be welded, the webs flutter or expand and contract when the speed is changed, with the result that a welding failure easily occurs.

Hence, an object of the present invention is to provide a web welding system and a welding method in which a welding failure is unlikely to occur.

A web welding system of the present invention includes: a transport device 3 that transports a work W in a state where a plurality of webs of the work W are overlaid on each other; an anvil roller 10 that includes an anvil 11, 12 which intermittently makes contact with a first surface W1 of the work W being transported; an ultrasonic horn 21, 22 that is opposite a second surface W2 of the work W and that cooperates with the anvil 11, 12 to apply vibration energy to the work W so as to intermittently weld the plurality of webs; a speed changing device 4 that lowers a transport speed of the work W supplied between the horn 21, 22 and the anvil 11, 12 when the welding is performed; and a pressing device 5 that presses the first surface W1 of the work W to the anvil 11, 12 when the welding is performed.

A web welding method using the welding system described above includes: a step of supplying the work W between the horn 21, 22 and the anvil 11, 12 while changing the transport speed of the work W with the speed changing device 4; a step of welding the plurality of webs between the horn 21, 22 and the anvil 11, 12 when the transport speed of the work W is lowered and a step of pressing, with the pressing device 5, the first surface W1 of the work W to the anvil 11, 12 when the welding is performed.

According to the present invention, the pressing device presses the work to the anvil, and thus it is possible to decrease the influence of the flutter or the expansion and contraction of the work and thereby to reduce a welding failure.

DESCRIPTION OF EMBODIMENTS

Figure 1:
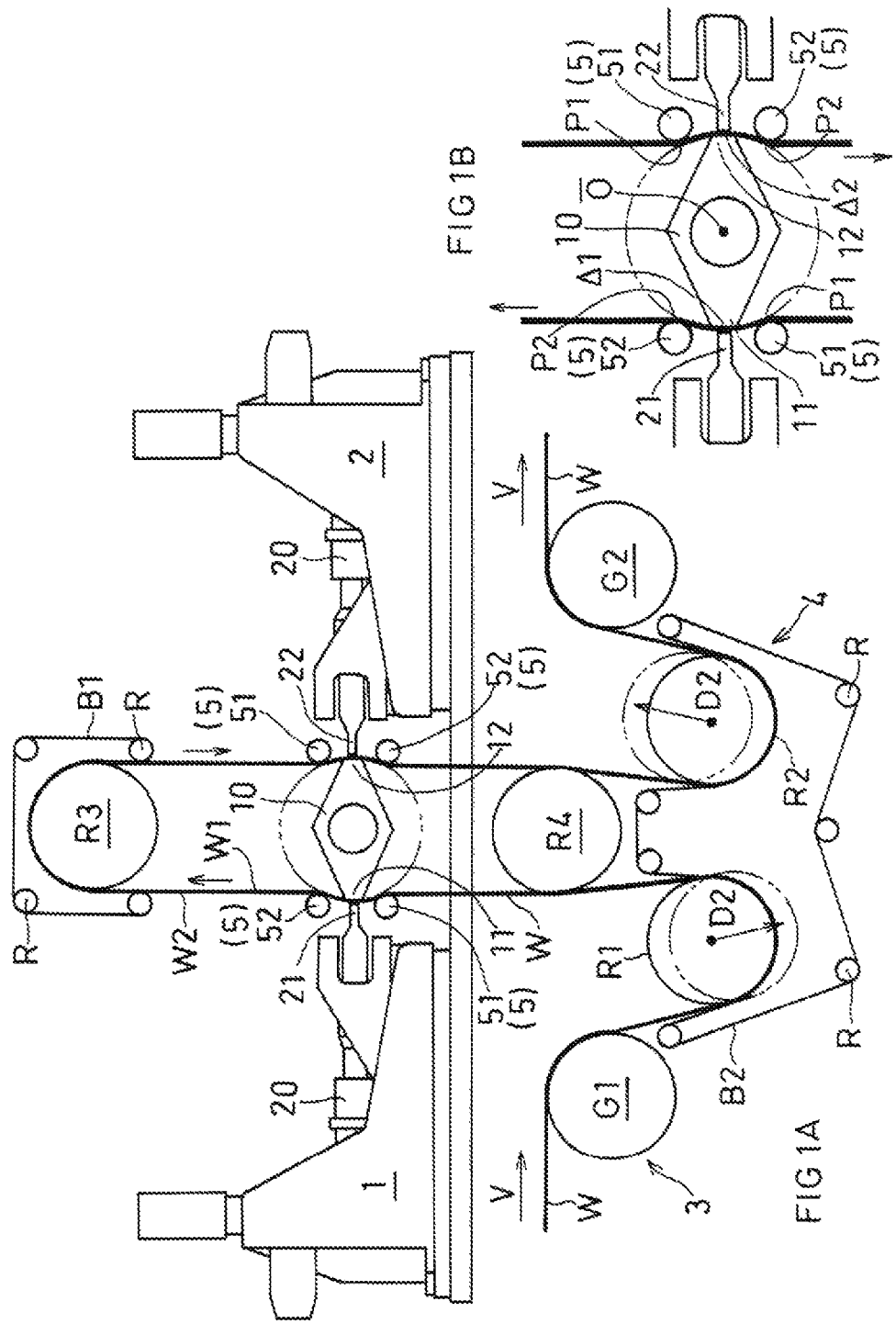
FIG. 1A is a schematic configuration view showing a welding system when welding is performed according to an embodiment of the present invention and FIG. 1B is an enlarged view of an anvil roller.

In a preferred system, the pressing device 5 includes a first pressing roller 51 that is arranged on an upstream side in the transport direction of the work W and that makes contact with the second surface W2 and a second pressing roller 52 that is arranged on a downstream side in the transport direction of the work W and that makes contact with the second surface W2, and the horn 21, 22 is arranged between the first pressing roller 51 and the second pressing roller 52.

In this case, when the anvil rotates to a position between the first pressing roller and the second pressing roller, the work is pressed to the anvil with the two pressing rollers, and thus the webs are welded, with the horn, between the horn and the anvil. Hence, the work is unlikely to flutter or expand and contract when the welding is performed.

In a further preferred system, the anvil 11, 12 makes contact with the work W between a first point P1 where the work W makes contact with the first pressing roller 51 and a second point P2 where the work W makes contact with the second pressing roller 52 such that the pressing device 5 presses the first surface W1 of the work W to the anvil 11, 12.

In this case, the anvil makes contact with the work between the first point and the second point, and in a state where the anvil is pressed to the work, the horn welds the work between the horn and the anvil.

In a preferred system, a pair of the horns 21, 22 are provided around the anvil roller 10, the anvil roller 10 includes a plurality of the anvils 11, 12 such that the plurality of the anvils 11, 12 correspond to the pair of the horns 21, 22, the transport device 3 further includes a reverse roller R3 which transports the work W such that the work W welded with one of the horns is welded with the other horn and the system includes a belt B1 that transports the work W while sandwiching the work W with the reverse roller R3.

In this case, the belt sandwiches the work with the reverse roller, and thus it is possible to decrease the flutter of the work on the surface of the reverse roller.

In a further preferred system, the speed changing device 4 includes a first dancer roller R1 that receives the work W from the upstream side to supply the work W to the anvil roller 10, a second dancer roller R2 that receives the work W from the anvil roller 10 to transport the work W to the downstream side and another belt B2 (separate from the belt B1) that transports the work W while sandwiching the work W with both the first and second dancer rollers R1 and R2.

In this case, the belt sandwiches the work with the first and second dancer rollers R1 and R2, and thus it is possible to decrease the flutter of the work on the surface of the dancer rollers.

In a preferred welding method, the pressing device 5 includes a first pressing roller 51 and a second pressing roller 52 that respectively make contact with the work W on upstream and downstream sides of the horn 21, 22, and when the anvil roller 10 rotates and the anvil 11, 12 is opposite (faces) the horn 21, 22 through the work W, the anvil 11, 12 protrudes to the side of the horn beyond the first and second pressing rollers 51 and 52 to apply tension to the work W between the first and second pressing rollers 51 and 52 so as to press the first surface W1 of the work W to the anvil 11 and 12.

As described above, the anvil makes contact with the work to which the tension is applied between the first and second pressing rollers, with the result that the structure of the pressing device is prevented from being complicated.

Any feature illustrated and/or depicted in conjunction with one of the aforementioned aspects or the following embodiments may be used in the same or similar form in one or more of the other aspects or other embodiments, and/or may be used in combination with, or in place of, any feature of the other aspects or embodiments.

Embodiments

The present invention will be understood more clearly from the following description of preferred embodiments taken in conjunction with the accompanying drawings. Note however that the embodiments and the drawings are merely illustrative and should not be taken to define the scope of the present invention. The scope of the present invention shall be defined only by the appended claims. In the accompanying drawings, like reference numerals denote like components throughout the plurality of figures.

An embodiment of the present invention will be described below with reference to drawings.

In the following discussion, an outline of a welding system of the present invention will first be described, and a speed changing device 4 provided in the welding system will then be described.

Figure 3:
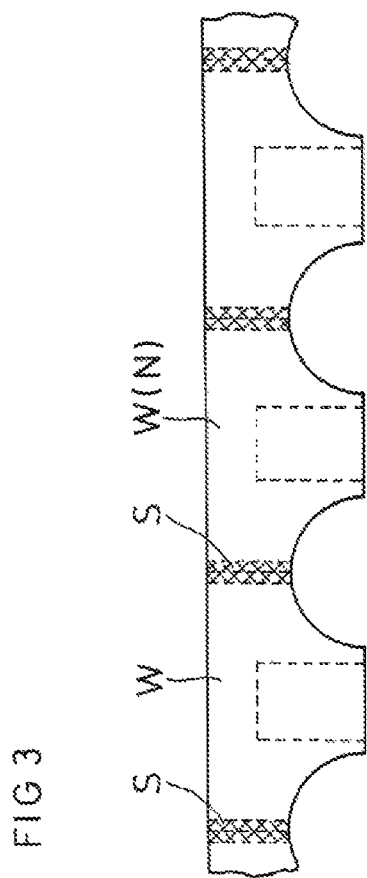
FIG. 3 is a schematic front view showing an example of a work before being cut into individual products.

The present system includes: the transport device 3 of FIG. 1A that transports a work W like a wearing article including a plurality of webs N shown in FIG. 3 and overlaid on each other; and a pair of ultrasonic welding devices 1 and 2 that weld the webs N being transported.

In FIG. 1A, the ultrasonic welding devices 1 and 2 include: an anvil roller 10 that includes a pair of anvils 11 and 12; first and second ultrasonic horns 21 and 22 that cooperate with the pair of anvils 11 and 12 to apply vibration energy to the work W; and a pair of sonic devices 20 and 20 that generate ultrasonic vibration in the ultrasonic horns 21 and 22. The anvils 11 and 12 intermittently make contact with the first surface W1 of the work W.

High-frequency mechanical vibration is applied to the horns 21 and 22, and thus the webs that pass between the horns 21 and 22 and the anvils 11 and 12 are welded together by frictional heat. The horns 21 and 22 are opposite (face) the second surface W2 of the work W, and cooperate with the anvils 11 and 12 to apply the vibration energy to the work W so as to weld the webs.

As the ultrasonic horns 21 and 22, for example, ultrasonic horns disclosed in JP 10-513128 W may be used.

The work W is formed by overlaying a plurality of thermoplastic webs that need to be welded together. The welding regions S of the work W shown in FIG. 3 and sealed with the sonic devices 20 and 20 are, for example, the end portions of a product like disposable underwear (an example of the wearing article).

The pair of anvils 11 and 12 in FIG. 1B are provided symmetrically with respect to the axis line (line extending along the rotation center O of the anvil 11) of the anvil roller 10. In other words, the pair of anvils 11 and 12 are provided in the anvil roller 10 with a pitch of 180°. The pair of ultrasonic horns 21 and 22 are arranged such that one of the pair of anvils 11 and 12 can be opposite (face) the first ultrasonic horn 21 and that the other of the pair of anvils 11 and 12 can be simultaneously opposite (face) the second ultrasonic horn 22.

In a state where the pair of anvils 11 and 12 are respectively opposite the first and second ultrasonic horns 21 and 22, the pair of ultrasonic horns 21 and 22 simultaneously apply the vibration energy to the work W. Hence, the work W (webs) is simultaneously welded at two places.

In FIGS. 1A and 1B, the transport device 3 transports the work W such that the work W passes through a first gap Δ1 between the anvil roller 10 and the first ultrasonic horn 21 and thereafter passes through a second gap Δ2 between the anvil roller 10 and the second ultrasonic horn 22. The transport device 3 includes a reverse roller R3, the speed changing device 4 which will be described in detail later and the like. The work W which has passed through the first gap Δ1 (FIG. 1B) moves along the outer circumferential surface of the reverse roller R3 and is thereafter transported into the second gap Δ2 (FIG. 1B).

The speed changing device 4 includes first and second dancer rollers R1 and R2 and a drive roller 4R. The first dancer roller R1 receives the work W that moves in from the upstream side, and ejects the work W toward the first gap Δ1 (FIG. 1B). The second dancer roller R2 receives the work W that is ejected from the second gap Δ2 (FIG. 1B), and ejects the work W toward the downstream side.

The speed changing device 4 reciprocates (swings) the first and second dancer rollers R1 and R2 as indicated by virtual and solid lines. The drive roller R4 rotates the first and second dancer rollers R1 and R2 at the same rotation speed (peripheral speed).

On the upstream side of the first dancer roller R1, a first guide roller G1 is rotatably provided. On the downstream side of the second dancer roller R2, a second guide roller G2 is rotatably provided. The first guide roller G1 guides the work W that moves toward the first dancer roller R1. On the other hand, the second guide roller G2 guides the work W that moves out from the second dancer roller R2. In a position above the area between both the dancer rollers R1 and R2, the drive roller R4 is arranged. The five rollers R1, R2, G1, G2 and R4 described above are driven by the drive roller R4 to rotate synchronously through an unillustrated timing belt.

A drive device for the five rollers is disclosed in WO 2005/080065 A1, the entire disclosure of which is incorporated herein by reference.

The speed changing device 4 transports the work W at high speed and at low speed alternately and repeatedly. In the high-speed transport, the moving speed of the work W between the dancer rollers R1 and R2 is higher than the speed V of the work W that moves in the first dancer roller R1. On the other hand, in the low-speed transport, the moving speed of the work W between the dancer rollers R1 and R2 is lower than the speed V.

Figure 2:
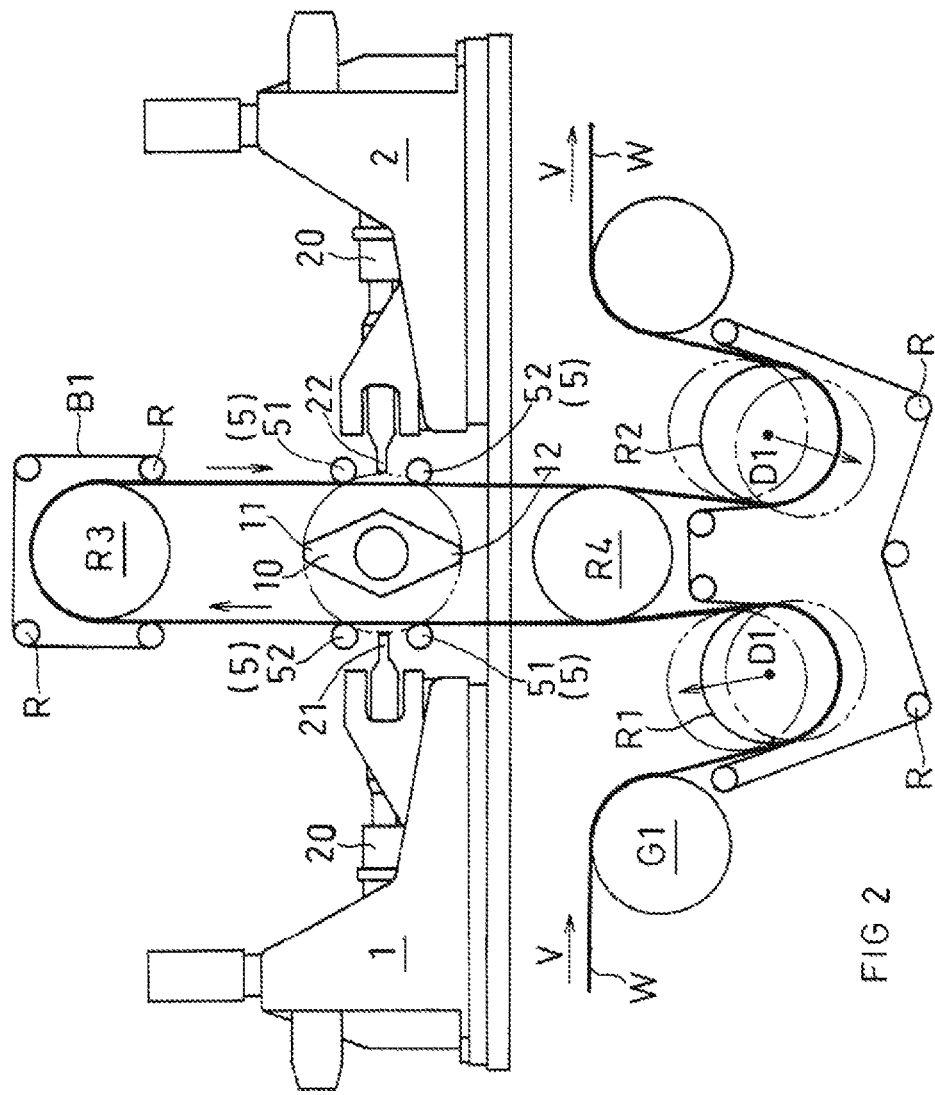
FIG. 2 is a schematic configuration view showing the welding system when the welding is not performed.

Specifically, in the high-speed transport of FIG. 2, both the dancer rollers R1 and R2 are moved such that, as indicated by arrows D1, the first dancer roller R1 moves close to the anvil roller 10 and that the second dancer roller R2 simultaneously moves away from the anvil roller 10, with the result that the work W is transported at high speed between both the dancer rollers R1 and R2.

On the other hand, in the low-speed transport of FIG. 1A, both the dancer rollers R1 and R2 are moved such that, as indicated by arrows D2, the first dancer roller R1 moves away from the anvil roller 10 and that the second dancer roller R2 simultaneously moves close to the anvil roller 10, with the result that the work W is transported at low speed between both the dancer rollers R1 and R2.

In this way, when the anvils 11 and 12 of FIG. 1A are respectively opposite the first and second ultrasonic horns 21 and 22, control is performed such that the speed of the work W between the first dancer roller R1 and the second dancer roller R2 is lower than the speed V of the work W which moves in the first dancer roller R1, and the welding is performed by ultrasonic energy.

As described above, when the horns 21 and 22 apply the vibration energy to the work W, the speed of the work W passing between the horns 21 and 22 and the anvils 11 and 12 is low, and thus the time during which the vibration energy is received is increased, with the result that energy received by the work W per unit area is increased. Hence, the reliability of the welding is enhanced.

The present welding system includes a pressing device 5 that presses the first surface W1 of the work W to the anvils 11 and 12 when the welding is performed. The pressing device 5 includes: first pressing rollers 51 that are arranged on the upstream side in the transport direction of the work W and that make contact with the second surface W2; and second pressing rollers 52 that are arranged on the downstream side in the transport direction of the work W and that make contact with the second surface W2. Between the first pressing rollers 51 and the second pressing rollers 52, the horns 21 and 22 are arranged.

In FIG. 1B, the anvils 11 and 12 make contact with the work W between first points P1 where the work W makes contact with the first pressing rollers 51 and second points P2 where the work W makes contact with the second pressing rollers 52, and thus the pressing device 5 presses the first surface W1 of the work W to the anvils 11 and 12.

In FIG. 1B, as indicated by a chain double-dashed line, the anvils 11 and 12 rotate about the rotation center O. The pressing rollers 51 and 52 are arranged close to the outside of the chain double-dashed line.

The present system of FIG. 1A further includes a first belt B1 and a second belt B2. The first belt B1 is an endless belt that is guided by a plurality of guide rollers R, and transports the work W while sandwiching the work W with the reverse roller R3. The second belt B2 is an endless belt that is guided by a plurality of guide rollers R, and transports the work W while sandwiching the work W with the first and second dancer rollers R1 and R2.

The control of the present system will then be described.

Both the dancer rollers R1 and R2 repeatedly reciprocate (swing) in the directions of the arrows D1 and D2, and thus the high-speed transport and the low-speed transport are repeated.

In FIG. 1A, when the anvils 11 and 12 are respectively opposite the first and second ultrasonic horns 21 and 22, the sonic devices 20 are controlled such that the pair of ultrasonic horns 21 and 22 apply the vibration energy to the work W, and thus the work W is welded.

On the other hand, the speeds of the drive roller R4 and the reverse roller R3 are changed synchronously such that the peripheral speeds of the drive roller R4 and the reverse roller R3 are equal to each other. The speeds of the drive roller R4 and the anvil roller 10 are periodically changed such that, when the work W is welded, the peripheral speeds of the anvil roller 10 and the drive roller R4 are equal to each other. In this way, control is performed according to the movements of the dancer rollers R1 and R2 such that the peripheral speeds of the drive roller R4 and the reverse roller R3, the peripheral speed of the anvil roller 10 when the work W is welded and the transport speed of the work W between the first dancer roller R1 and the second dancer roller R2 are equal to each other.

The operation of the present system will then be described.

The work W of FIG. 1A moves from the first guide roller G1 along the outer circumferential surface of the first dancer roller R1 at a substantially constant speed V, passes through the first and second gaps $\Delta 1$ and $\Delta 2$, moves along the outer circumferential surface of the second dancer roller R2 and is thereafter transported along the second guide roller G2 at the substantially constant speed V. The work W between the first dancer roller R1 and the second dancer roller R2 is supplied into the gaps $\Delta 1$ and $\Delta 2$ (FIG. 1B) between the horns and the anvils while the speed of the work W is being changed with the speed changing device 4.

Specifically, as shown in FIG. 1A, the first dancer roller R1 is moved in the direction of the arrow D2 such that the length of the work W between the first dancer roller R1 and the first gap $\Delta 1$ (FIG. 1B) is increased, and the second dancer roller R2 is moved in the direction of the arrow D2 such that the length of the work W between the second dancer roller R2 and the second gap $\Delta 2$ (FIG. 1B) is decreased. In this way, the speed of the work W between the first dancer roller R1 and the second dancer roller R2 is lower than the speed V of the work W that moves in the first dancer roller R1.

When the work W is transported at low speed, the anvils 11 and 12 of the anvil roller 10 are opposite the ultrasonic horns 21 and 22, the sonic devices 20 are operated and thus the welding regions S of the work W of FIG. 3 adjacent to each other are simultaneously welded (sealed).

As shown in FIG. 2, the first dancer roller R1 is moved in the direction of the arrow D1 such that the length of the work W between the first dancer roller R1 and the first gap $\Delta 1$ (FIG. 1B) is decreased, and the second dancer roller R2 is moved in the direction of the arrow D1 such that the length of the work W between the second dancer roller R2 and the second gap $\Delta 2$ (FIG. 1B) is increased. In this way, the speed of the work W between the first dancer roller R1 and the second dancer roller R2 is higher than the speed V of the work W that moves in the first dancer roller R1.

When the welding of FIGS. 1A and 1B is performed, the pressing device 5 presses the first surface W1 of the work W to the anvils 11 and 12.

Specifically, when the anvil roller 10 rotates and the anvils 11 and 12 are opposite the horns through the work W, the anvils 11 and 12 protrude to the sides of the horns beyond the first and second pressing rollers 51 and 52 to apply tension to the work W between the first pressing rollers 51 and the second pressing rollers 52 so as to press the first surface W1 of the work W to the anvils 11 and 12.

Hence, in a state where the desired tension is applied to the work W, the webs N (FIG. 3) are welded together. Therefore, in a state where the work W does not flutter or expand and contract, the webs N (FIG. 3) of the work W are welded together, with the result that a welding failure is unlikely to occur.

Although as described above, the preferred embodiment has been described with reference to the drawings, a person skilled in the art easily conceives various variations and modifications from the present specification within an obvious range.

For example, the reverse roller does not necessarily need to be provided.

Furthermore, the reverse roller may be supported by a support means through a means that can finely adjust the position of the axis center.

The drive roller R4 does not need to be in contact with the work W.

The dancer rollers may swing not vertically but laterally.

Hence, the variations and modifications as described above are interpreted to be within the scope of the present invention defined by the scope of claims.

INDUSTRIAL APPLICABILITY

The welding system of the present invention can be utilized, for example, not only for the production facilities of disposable wearing articles such as disposable pants, diapers and sanitary items but also for the production facilities of medical wound dressing materials and the like.

REFERENCE SIGNS LIST 1, 2: first and second ultrasonic welding devices
10: anvil roller
11, 12: first and second anvils
20: sonic device
21, 22: first and second ultrasonic horns
3: transport device
4: speed changing device
51: first pressing roller
52: second pressing roller
B1, B2: belt
O: rotation center
P1: first point
P2: second point
R1: first dancer roller
R2: second dancer roller
R3: reverse roller
R4: drive roller
W: work
W1: first surface
W2: second surface
Δ1, Δ2: gap

The invention claimed is:
1. A web welding system comprising:
a transport device that transports a work in a state where a plurality of webs of the work are overlaid on each other;
an anvil roller that includes an anvil which intermittently makes contact with a first surface of the work being transported;
an ultrasonic horn that is opposite a second surface of the work and that cooperates with the anvil to apply vibration energy to the work so as to intermittently weld the webs;
a speed changing device that lowers a transport speed of the work supplied between the horn and the anvil when the welding is performed; and
a pressing device that presses the first surface of the work to the anvil when the welding is performed, wherein the pressing device includes:
a first pressing roller that is arranged on an upstream side in a transport direction of the work and that makes contact with the second surface, and
a second pressing roller that is arranged on a downstream side in the transport direction of the work and that makes contact with the second surface;
wherein the horn is arranged between the first pressing roller and the second pressing roller; and
wherein the anvil roller and the first and second pressing rollers are configured such that:
(i) when the anvil roller rotates and the anvil faces the horn through the work, the anvil protrudes to a side of the horn beyond the first and second pressing rollers to apply tension to the work between the first and second pressing rollers so as to press the first surface of the work to the anvil, and
(ii) when the anvil roller rotates and the anvil faces in the transport direction of the work, no tension is applied to the work between the first and second pressing rollers and the work linearly extends in the transport direction.

2. The web welding system according to claim 1, wherein the anvil makes contact with the work W between a first point where the work makes contact with the first pressing roller and a second point where the work makes contact with the second pressing roller such that the pressing device presses the first surface of the work to the anvil.

3. The web welding system according to claim 1, wherein the ultrasonic horn is provided in a pair,
the pair of the ultrasonic horns are provided around the anvil roller,
the anvil roller includes a plurality of the anvils such that the plurality of the anvils correspond to the pair of the horns and
the transport device further includes a reverse roller which transports the work such that the work welded with one of the pair of the horns is welded with another one of the pair of the horns.

4. The web welding system according to claim 3, comprising:
a belt that transports the work while sandwiching the work with the reverse roller.

5. The web welding system according to claim 4, wherein the speed changing device includes
a first dancer roller that receives the work from the upstream side to supply the work to the anvil roller,
a second dancer roller that receives the work from the anvil roller to transport the work to the downstream side and
another belt that transports the work while sandwiching the work with the first dancer roller and with the second dancer roller.

6. A web welding method using the welding system according to claim 1, the web welding method comprising:
a step of supplying the work W between the horn and the anvil while changing the transport speed of the work with the speed changing device;
a step of welding the plurality of webs between the horn and the anvil when the transport speed of the work is lowered and
a step of pressing, with the pressing device, the first surface of the work to the anvil when the welding is performed.

7. The web welding method according to claim 6,
wherein the pressing device includes a first pressing roller making contact with the work on an upstream side of the horn and
a second pressing roller making contact with the work on a downstream side of the horn, and
when the anvil roller rotates and the anvil faces the horn through the work, the anvil protrudes to a side of the horn beyond the first and second pressing rollers to apply tension to the work between the first and second pressing rollers so as to press the first surface of the work to the anvil.

8. The web welding system according to claim 1,
wherein the ultrasonic horn is provided in a pair,
the pair of the ultrasonic horns are provided around the anvil roller,
the anvil roller includes a plurality of the anvils such that the plurality of the anvils correspond to the pair of the horns and
the transport device further includes a reverse roller which transports the work such that the work welded with one of the pair of the horns is welded with another one of the pair of the horns.

9. The web welding system according to claim 8, comprising:
a belt that transports the work while sandwiching the work with the reverse roller.

10. The web welding system according to claim 9,
wherein the speed changing device includes
a first dancer roller that receives the work from the upstream side to supply the work to the anvil roller,
a second dancer roller that receives the work from the anvil roller to transport the work to the downstream side and
another belt that transports the work while sandwiching the work with the first dancer roller and with the second dancer roller.

11. The web welding system according to claim 2,
wherein the ultrasonic horn is provided in a pair,
the pair of the ultrasonic horns are provided around the anvil roller,
the anvil roller includes a plurality of the anvils such that the plurality of the anvils correspond to the pair of the horns and
the transport device further includes a reverse roller which transports the work such that the work welded with one of the pair of the horns is welded with another one of the pair of the horns.

12. The web welding system according to claim 11, comprising:
a belt that transports the work while sandwiching the work with the reverse roller.

13. The web welding system according to claim 12,
wherein the speed changing device includes
a first dancer roller that receives the work from the upstream side to supply the work to the anvil roller,
a second dancer roller that receives the work from the anvil roller to transport the work to the downstream side and
another belt that transports the work while sandwiching the work with the first dancer roller and with the second dancer roller.

* * * * *